US00PP21559P2

(12) United States Plant Patent
Ferguson et al.

(10) Patent No.: US PP21,559 P2
(45) Date of Patent: Dec. 7, 2010

(54) STRAWBERRY PLANT NAMED 'DRISSTRAWTHIRTEEN'

(50) Latin Name: *Fragaria×ananassa*
Varietal Denomination: DrisStrawThirteen

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/586,772

(22) Filed: Sep. 28, 2009

(51) Int. Cl.
*A01H 5/00* (2006.01)

(52) U.S. Cl. ..... Plt./209
(58) Field of Classification Search ..... Plt./208, Plt./209

See application file for complete search history.

*Primary Examiner*—Susan B McCormick Ewoldt
(74) *Attorney, Agent, or Firm*—Jondle & Associates, P.C.

(57) ABSTRACT

This invention relates to a new and distinct cultivar of strawberry plant named 'DrisStrawThirteen.' The new cultivar is primarily characterized by having large-sized, fruit with strong sweetness and weak acidity and having a plant with resistance to powdery mildew and moderate resistance to Strawberry Mottle Virus, wind, drought, high temperatures, high pH, high soil salt levels and water logging.

3 Drawing Sheets

Genus and species: *Fragaria×ananassa.*
Variety denomination: 'DrisStrawThirteen'.

BACKGROUND OF THE NEW PLANT

The present invention relates to a new and distinct strawberry cultivar designated 'DrisStrawThirteen' and botanically known as *Fragaria×ananassa*. This new strawberry cultivar was discovered in Ventura, Calif. in October 2005 and originated from a cross between the proprietary female parent '2K297' (unpatented) and the male parent 'Driscoll Ojai' (U.S. Plant Pat. No. 18,575). The original seedling of the new cultivar was first asexually propagated at a nursery in Shasta County, Calif.

'DrisStrawThirteen' was subsequently asexually propagated in Shasta County, Calif. and underwent further testing in Ventura County, Calif. for four years. The present invention has been found to retain its distinctive characteristics through successive asexual propagations via stolons and tissue culture.

DESCRIPTION OF THE PHOTOGRAPHS

The accompanying color photographs show typical specimens of the new cultivar at various stages of development as nearly true as it is possible to make in color reproductions. The photographs were taken from 6-month-old plants.

DESCRIPTION OF THE NEW CULTIVAR

Figure 1:
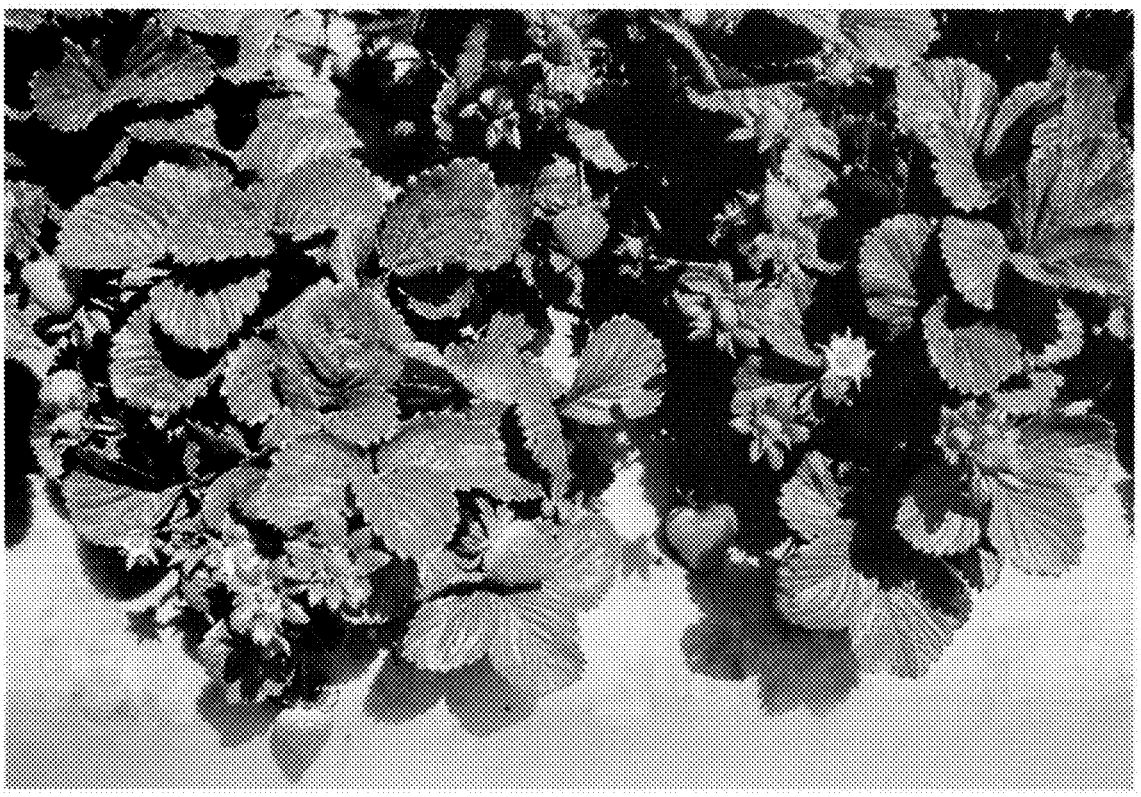
FIG. 1 shows overall plant habit including fruit at various stages of development.
Figure 2:
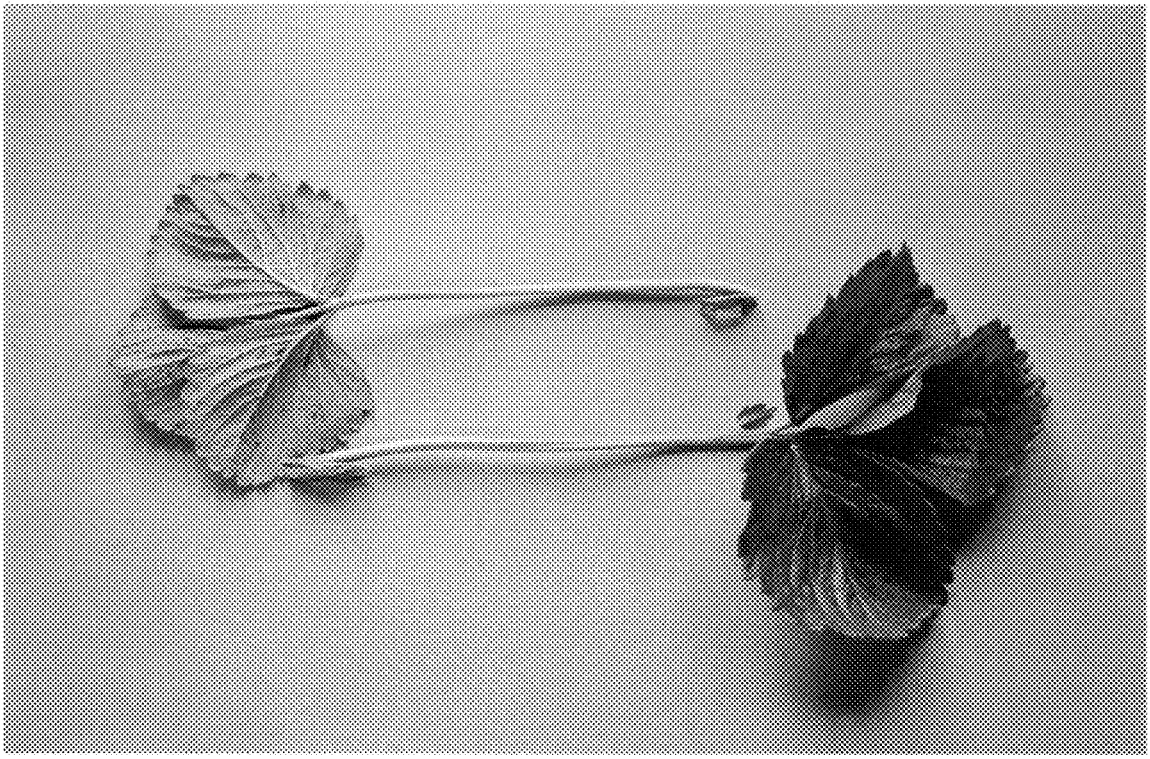
FIG. 2 shows leaves of the plant with three leaflets.
Figure 3:
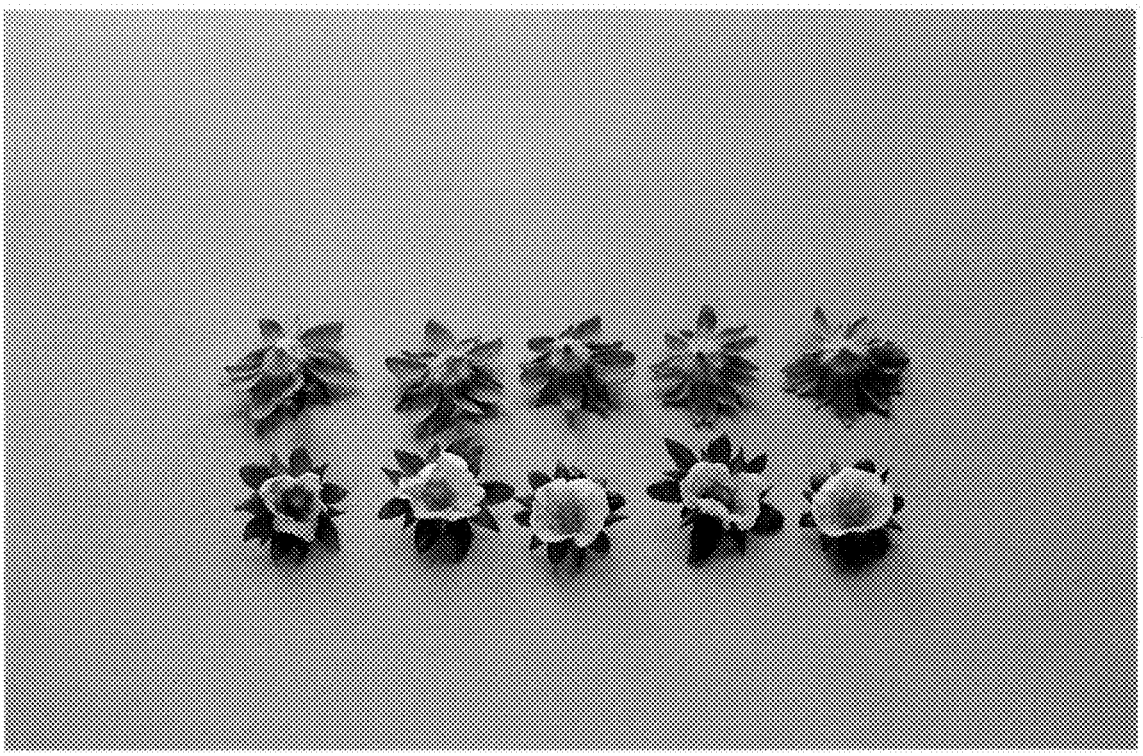
FIG. 3 shows both the upper side and underside of several of the flowers.
Figure 4:
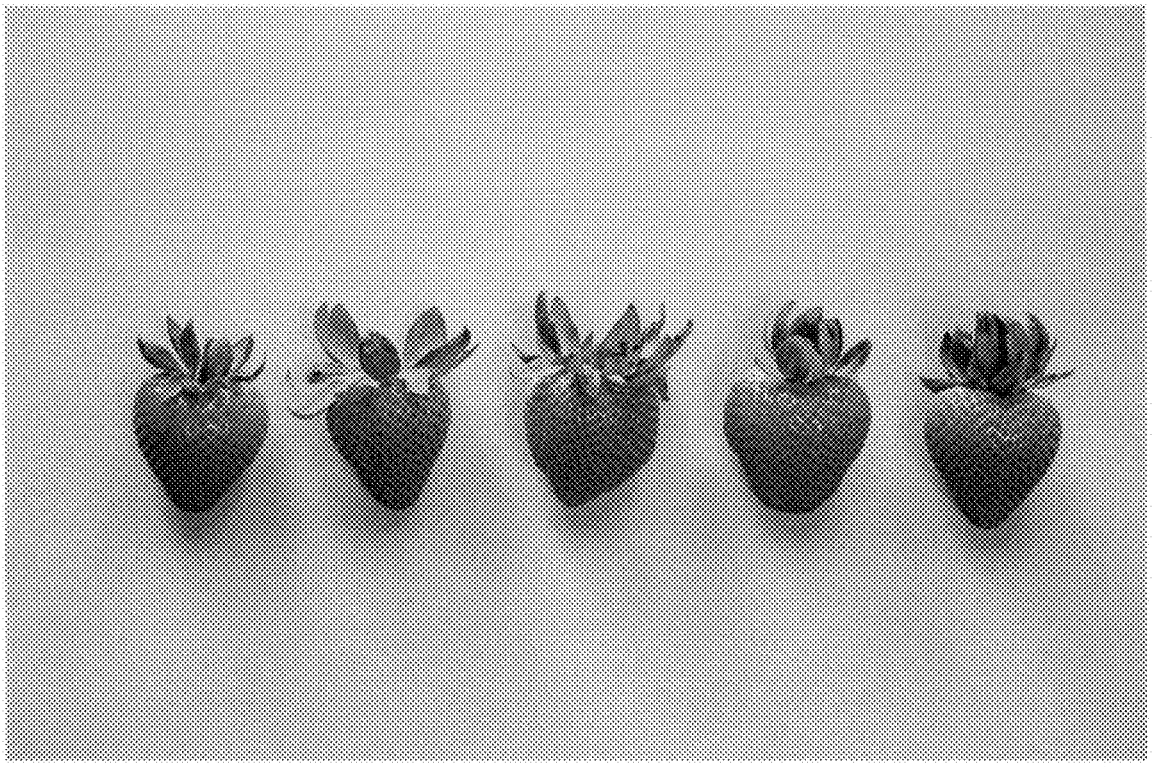
FIG. 4 shows the whole fruit.
Figure 5:
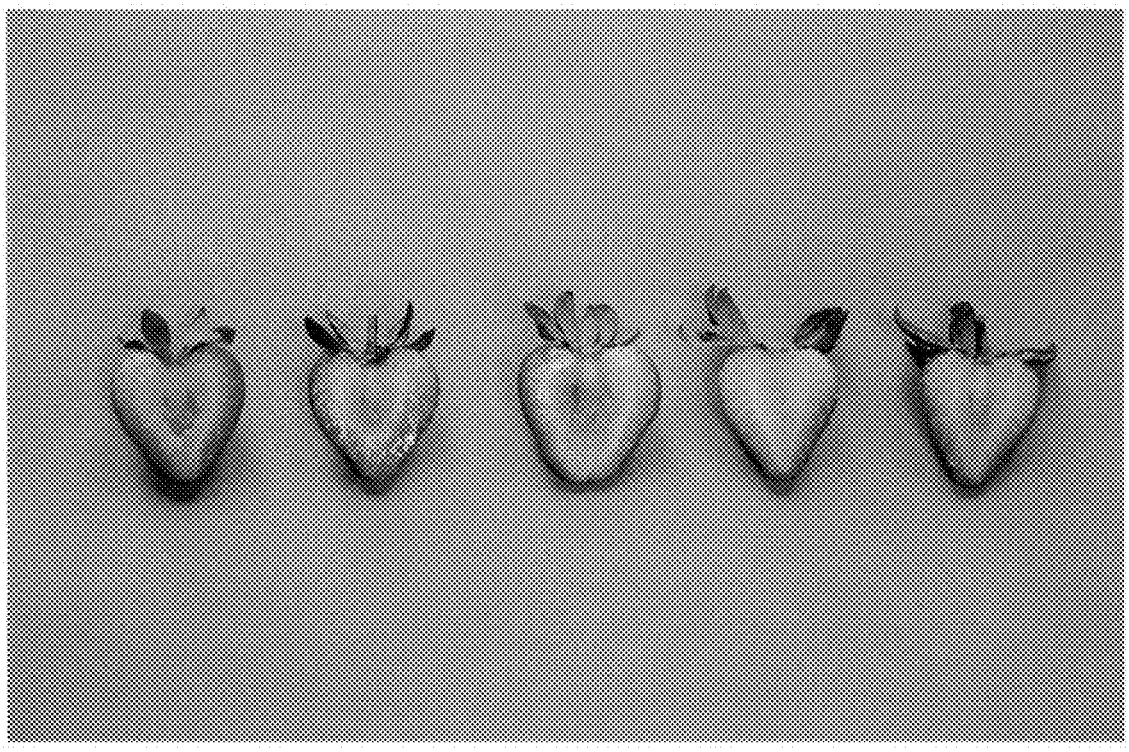
FIG. 5 shows the fruit in longitudinal cross-section.

The following description of 'DrisStrawThirteen' is based on observations taken in Ventura, Calif. from 2005 to 2009.

This description is in accordance with UPOV terminology. Color designations, color descriptions, and other phenotypical descriptions may deviate from the stated values and descriptions depending upon variation in environmental, seasonal, climatic and cultural conditions. 'DrisStrawThirteen' has not been observed under all possible environmental conditions. The botanical description of 'DrisStrawThirteen' was taken from 6-month-old plants and the botanical descriptions of the comparison varieties, 'Driscoll Ojai' and 'Driscoll El Dorado' (U.S. Plant Pat. No. 16,238), were also taken from 6-month-old plants. Color terminology follows The Royal Horticultural Society Colour Chart, London (R.H.S.) (2001).

DETAILED BOTANICAL DESCRIPTION

Table 1 shows selected plant characteristics of the new variety compared with plant characteristics of 'Driscoll Ojai' and 'Driscoll El Dorado.' Plant characteristics include plant habit, terminal leaflet margin profile, insertion of achenes, and fruit production.

TABLE 1

| Characteristic | 'DrisStrawThirteen' | 'Driscoll Ojai' | 'Driscoll El Dorado' |
|---|---|---|---|
| Plant habit | Globose | Globose | Flat globose |
| Terminal leaflet margin profile | Revolute to flat | Revolute | Revolute and flat |
| Insertion of achenes | Level with surface | Level with surface | Below surface |
| Fruit production, grams/plant | 473.7 | 435.4 | 707.8 |

Table 2 shows plant characteristics of the new variety compared with plant characteristics of the commercial varieties 'Driscoll Ojai' and 'Driscoll El Dorado.' Plant characteristics include plant height, diameter, number of crowns per plant, habit, the density of individual plants and the vigor.

TABLE 2

| Characteristic | 'DrisStrawThirteen' | 'Driscoll Ojai' | 'Driscoll El Dorado' |
|---|---|---|---|
| Plant height (cm) | 20.6 | 22.9 | 19.0 |
| Plant diameter (cm) | 36.0 | 35.4 | 34.7 |
| Number of crowns/plant | 3 | 3 | 3 |
| Habit | Globose | Globose | Flat globose |
| Density of individual plant | Medium | Medium | Medium |
| Vigor | Very strong | Medium | Medium |

Table 3 shows leaf characteristics of the new cultivar compared with leaf characteristics of 'Driscoll Ojai' and 'Driscoll El Dorado.' Leaf characteristics include terminal leaflet length and width in centimeters, length to width ratio, number of teeth per terminal leaflet, shape of teeth, color of upper side and underside of leaf, leaf shape in cross section, leaf blistering, leaf glossiness, number of leaflets, terminal leaflet margin, terminal leaflet length to width ratio, overall leaf shape and shape of leaf apex and base.

TABLE 3

| Leaf Characteristic | 'DrisStrawThirteen' | 'Driscoll Ojai' | 'Driscoll El Dorado' |
|---|---|---|---|
| Terminal leaflet length (cm) | 8.0 | 7.4 | 7.6 |
| Terminal leaflet width (cm) | 7.4 | 6.7 | 6.8 |
| Terminal leaflet length/width ratio | 1.1 | 1.1 | 1.1 |
| No. teeth/terminal leaflet | 21 | 22 | 22 |
| Shape of teeth | Rounded | Rounded | Rounded |
| Color of upper surface of leaf | RHS 137A (Dark green) | RHS 147A (Dark yellow-green) | RHS 147A (Dark yellow-green) |
| Color of lower surface of leaf | RHS 148B (Medium yellow-green) | RHS 148C (Light yellow-green) | RHS 148B (Medium yellow-green) |
| Leaf shape in cross section | Slightly concave | Slightly convex | Slightly concave |
| Leaf blistering | Medium | Medium | Medium |
| Leaf glossiness | Strong | Medium | Medium |
| No. leaflets | 3 only | 3 only | 3 only |
| Terminal leaflet margin | Between revolute and flat | Revolute | Both revolute and flat |
| Terminal leaflet: length/width ratio | As long as broad | As long as broad | As long as broad |
| Terminal leaflet shape | Orbicular | Orbicular | Oval |
| Terminal leaflet base shape | Slightly oblique | Slightly oblique | Slightly oblique |
| Terminal leaflet apex shape | Rounded | Rounded | Rounded |

Table 4 shows information about the petiole, the petiolule, the bract, and the stipule of the new cultivar compared to 'Driscoll Ojai' and 'Driscoll El Dorado.' This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 4

| Characteristic | 'DrisStrawThirteen' | 'Driscoll Ojai' | 'Driscoll El Dorado' |
|---|---|---|---|
| Petiole length (cm) | 12.4 | 9.7 | 10.1 |
| Petiole diameter (cm) | 0.355 | 0.358 | 0.332 |
| Petiole pubescence | Medium | Medium | Medium |
| Petiole pose of hairs | Outwards | Outwards | Outwards |
| Petiole color | RHS 145A (Medium yellow-green) | RHS 145A (Medium yellow-green) | RHS 146D (Medium yellow-green) |
| Petiolule color | RHS 145A (Medium yellow-green) | RHS 145A (Medium yellow-green) | RHS 146D (Medium yellow-green) |
| Petiolule length (cm) | 6.93 | 6.35 | 6.19 |
| Petiolule diameter (cm) | 0.165 | 0.144 | 0.147 |
| Bract frequency | 1 | 1 | 0 |
| Stipule length (cm) | 3.2 | 3.7 | 3.0 |
| Stipule width (cm) | 1.073 | 1.204 | 1.074 |
| Stipule pubescence | Medium | Medium | Medium |
| Stipule anthocyanin coloration | RHS 150D (Light yellow-green) | RHS 142C (Light green) | RHS 149B (Medium yellow-green) |

Table 5 shows stolon characteristics of the new cultivar compared to 'Driscoll Ojai' and 'Driscoll El Dorado.' These characteristics include the number of stolons, average number of daughter plants, the anthocyanin coloration of the stolons, the thickness of the stolons, and the pubescence of the stolons.

TABLE 5

| Characteristic | 'DrisStrawThirteen' | 'Driscoll Ojai' | 'Driscoll El Dorado' |
|---|---|---|---|
| Stolon Number | Medium | Many | ND* |
| Average number of daughter plants | 50+ | 62 | 129 |
| Stolon Anthocyanin | RHS 59B (Dark red-purple) | RHS 61C (Medium red-purple) | RHS 59C (Dark red-purple) |
| Stolon Thickness | Thin | Medium | Thin |
| Stolon Pubescence | Sparse | Sparse | Medium |

*ND = Not determined

Table 6 shows inflorescence characteristics of the new cultivar compared to 'Driscoll Ojai' and 'Driscoll El Dorado.' These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 6

| Characteristic | 'DrisStrawThirteen' | 'Driscoll Ojai' | 'Driscoll El Dorado' |
|---|---|---|---|
| Inflorescence position relative to foliage | Between level with and above | Above | Above |

TABLE 6-continued

| Characteristic | 'DrisStrawThirteen' | 'Driscoll Ojai' | 'Driscoll El Dorado' |
|---|---|---|---|
| Time of flowering (50% of plants at first flower) | Medium | Medium | Medium |
| Flower size | Medium | Medium | Medium |
| Flower diameter (cm) | 2.688 | 3.289 | 2.773 |
| Petal shape | Orbicular | Orbicular | Orbicular |
| Petal spacing | Overlapping | Overlapping | Overlapping |
| Petal apex shape | Rounded | Rounded | Rounded |
| Petal margin | Entire | Entire | Entire |
| Petal base shape | Rounded | Rounded | Rounded |
| Petal length (cm) | 1.531 | 1.571 | 1.496 |
| Petal width (cm) | 1.464 | 1.621 | 1.570 |
| Petal length/width ratio | As long as broad | As long as broad | As long as broad |
| Typical and observed petal number | 6 | 6 | 7 |
| Petal color | RHS 155B (White) | RHS 155D (White) | RHS 155B (White) |
| Calyx diameter (cm) | 3.897 | 4.518 | 4.271 |
| Calyx diameter relative to corolla | Larger | Larger | Larger |
| Inner calyx diameter relative to outer | Same size | Same size | Same size |
| Sepal shape | Oval | Oval | Oval |
| Sepal apex shape | Convex | Convex | Convex |
| Sepal margin | Entire | Entire | Entire |
| Sepal length (cm) | 1.538 | 1.787 | 1.654 |
| Sepal width (cm) | 0.628 | 0.802 | 0.674 |
| Typical and observed sepal number | 12 | 13 | 15 |
| Receptacle color | RHS 154B (Light yellow-green) | RHS 1B (Medium green-yellow) | RHS 1A (Medium green-yellow) |
| Anther color | RHS 17A (Medium yellow-orange) | RHS 163B (Medium greyed-orange) | RHS 163A (Medium greyed-orange) |

Table 7 shows fruit characteristics of the new cultivar compared to 'Driscoll Ojai' and 'Driscoll El Dorado.' These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 7

| Characteristic | 'DrisStrawThirteen' | 'Driscoll Ojai' | 'Driscoll El Dorado' |
|---|---|---|---|
| Fruiting truss length (cm) | 22.1 | 20.7 | 18.7 |
| Fruiting truss length-general | Medium | Medium | Medium |
| Fruiting truss diameter (cm) at base of truss | 0.339 | 0.281 | 0.270 |
| Number of berries per fruiting truss | 1 | 1 | 1 |

TABLE 7-continued

| Characteristic | 'DrisStrawThirteen' | 'Driscoll Ojai' | 'Driscoll El Dorado' |
|---|---|---|---|
| Fruiting truss attitude | Prostrate | Prostrate | Prostrate |
| Fruiting truss color at base of truss | RHS 144A (Medium yellow-green) | RHS 144A (Medium yellow-green) | RHS 144B (Medium yellow-green) |
| Fruit length (cm) | 5.262 | 4.310 | 4.904 |
| Fruit width (cm) | 5.196 | 3.888 | 4.237 |
| Fruit length/width ratio | 1.0 | 1.1 | 1.2 |
| Fruit hollow length (cm) | 2.039 | 1.617 | 2.141 |
| Fruit hollow width (cm) | 0.968 | 0.903 | 1.412 |
| Fruit hollow length/width ratio | 2.1 | 1.8 | 1.5 |
| Fruit weight (g) | 28.7 | 26.7 | 26.1 |
| Relative fruit size | Large | Large | Large |
| Predominant fruit shape | Between conical and almost cylindrical | Conical | Conical and almost cylindrical |
| Difference in shape between primary & secondary fruits | Slight | Moderate | Slight |
| Band without achenes | Medium | Narrow | Absent or very narrow |
| Unevenness of fruit surface | Strong | Medium | Medium |
| Fruit skin color | RHS 46A (Dark red) | RHS 45A (Medium red) | RHS 46A (Dark red) |
| Evenness of fruit color | Even | Even | Slightly Uneven |
| Fruit glossiness | Medium | Medium | Medium |
| Insertion of achenes | Level with surface | Level with surface | Below surface |
| Achene coloration-sunward side of berry | RHS 185A (Dark greyed-purple) | RHS 178B (Dark greyed-red) | RHS 185A (Dark greyed-purple) |
| Achene coloration-shaded side of berry | RHS 153A (Medium yellow-green) | RHS 152D (Medium yellow-green) | RHS 153C (Medium yellow-green) |
| Achenes per berry | 358.7 | 234.5 | 215.3 |

Table 8 shows fruit characteristics of the new cultivar compared to 'Driscoll Ojai' and 'Driscoll El Dorado.' These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 8

| Characteristic | 'DrisStrawThirteen' | 'Driscoll Ojai' | 'Driscoll El Dorado' |
|---|---|---|---|
| Harvest maturity | Late December to mid-June | Late January to late May | Early January to late May |
| Insertion of calyx | Level | Level | Level |
| Pose of calyx segments | Reflexed | Reflexed | Reflexed |
| Size of calyx in relation to fruit | From same size to larger | Between same size and larger | Between same size and larger |
| Adherence of calyx | Strong | Strong | Strong |
| Firmness of flesh | Between soft and medium | Firm | Firm |
| Color of the flesh | RHS N155D (White) and RHS 45A (Dark Red) | RHS 155D (White) and RHS N30A (Dark orange-red) | RHS 155B (White) and RHS 42B (Medium red) |

TABLE 8-continued

| Characteristic | 'DrisStrawThirteen' | 'Driscoll Ojai' | 'Driscoll El Dorado' |
|---|---|---|---|
| Evenness of flesh color | Even | Even | Even |
| Distribution of flesh color | Marginal and central | Only marginal | Marginal and central |
| Hollow center | Between small and medium | Between small and medium | Between small and medium |
| Sweetness | Strong | Medium | Medium |
| Acidity | Weak | Medium | Medium |
| Texture when tasted | Fine | Medium | Medium |
| Type of bearing | Partially everbearing | Partially everbearing | Partially everbearing |
| Grams of fruit/plant | 473.7 | 435.4 | 707.8 |

Table 9 shows pest, stress and disease characteristics of the new cultivar compared to 'Driscoll Ojai' and 'Driscoll El Dorado'.

TABLE 9

| Pest, Stress or Disease | 'DrisStrawThirteen' | 'Driscoll Ojai' | 'Driscoll El Dorado' |
|---|---|---|---|
| *Lygus hesperus* (Lygus bug) | Moderately resistant | Susceptible | Susceptible |
| *Botrytis* fruit rot | Moderately susceptible | Moderately susceptible | Susceptible |
| Powdery mildew | Resistant | Moderately susceptible | Moderately resistant |
| *Verticillium* wilt | Moderately susceptible | Susceptible | Moderately susceptible |
| Strawberry mottle virus | Moderately resistant | Moderately resistant | Moderately resistant |
| *Xanthomonas fragariae* | Moderately susceptible | Moderately susceptible | Moderately susceptible |
| Drought | Moderately resistant | ND* | ND |
| High temperatures | Moderately resistant | ND | ND |
| Wind | Moderately resistant | ND | ND |
| High pH | Moderately resistant | ND | ND |
| High soil salt levels | Moderately resistant | ND | ND |
| Water logging | Moderately resistant | ND | ND |

*ND = Not determined

COMPARISON WITH PARENTAL AND COMMERCIAL CULTIVARS

When 'DrisStrawThirteen' is compared to the proprietary female parent '2K297' (unpatented), 'DrisStrawThirteen' has larger fruit with a softer texture than does '2K297.' In addition, 'DrisStrawThirteen' produces fruit three weeks earlier, has a more compact plant habit with darker foliage and is more rain tolerant than '2K297'.

When 'DrisStrawThirteen' is compared to the male parent 'Driscoll Ojai' (U.S. Plant Pat. No. 18,575), 'DrisStrawThirteen' produces fruit four weeks earlier than 'Driscoll Ojai'. In addition, 'DrisStrawThirteen' is more rain tolerant, has a more compact plant habit with darker foliage than 'Driscoll Ojai' and hides its fruit underneath the canopy whereas 'Driscoll Ojai' has a more upright plant habit and presents its fruit above the canopy.

We claim:

1. A new and distinct cultivar of strawberry plant as described and shown herein.

* * * * *